United States Patent
Karp et al.

(10) Patent No.: US 9,504,733 B2
(45) Date of Patent: Nov. 29, 2016

(54) REGULATION OF ENERGY METABOLISM AND OBESITY BY MODULATING A PROLIFERATION-INDUCING LIGAND (APRIL) OR APRIL SIGNALING

(71) Applicant: Children's Hospital Medical Center, Cincinnati, OH (US)

(72) Inventors: Christopher L. Karp, Seattle, WA (US); Senad Divanovic, Cincinatti, OH (US); Jessica L. Allen, Saxapahaw, NC (US)

(73) Assignee: Children's Hospital Medical Center, Cincinnati ( * ) Notice: Subject to any disclaimer, the term of this patent is extended or adjusted under 35 U.S.C. 154(b) by 0 days.

(21) Appl. No.: 14/252,498

(22) Filed: Apr. 14, 2014

(65) Prior Publication Data

US 2014/0221279 A1    Aug. 7, 2014

Related U.S. Application Data

(62) Division of application No. 13/364,776, filed on Feb. 2, 2012, now Pat. No. 8,735,347.

(60) Provisional application No. 61/438,964, filed on Feb. 2, 2011.

(51) Int. Cl.
| | |
|---|---|
| A61K 38/18 | (2006.01) |
| C07K 14/475 | (2006.01) |
| C07K 14/52 | (2006.01) |
| C07K 14/525 | (2006.01) |
| A61K 38/19 | (2006.01) |
| A61P 3/04 | (2006.01) |
| A61K 38/17 | (2006.01) |
| A61K 31/7088 | (2006.01) |
| A61K 31/715 | (2006.01) |
| A61K 31/739 | (2006.01) |

(52) U.S. Cl.
CPC ........... *A61K 38/19* (2013.01); *A61K 31/7088* (2013.01); *A61K 31/715* (2013.01); *A61K 31/739* (2013.01); *A61K 38/1793* (2013.01); *A61K 38/191* (2013.01); *C07K 14/525* (2013.01)

(58) Field of Classification Search
CPC .. A61K 2300/00; A61K 38/19; A61K 38/17; A61K 38/1709; A61K 38/18; C07K 14/475; C07K 14/52; C07K 14/525; C07K 14/47
See application file for complete search history.

(56) References Cited

U.S. PATENT DOCUMENTS

| | | | |
|---|---|---|---|
| 7,553,930 B2 | 6/2009 | Desjarlais | |
| 7,635,677 B2 | 12/2009 | Ambrose | |
| 2006/0014248 A1* | 1/2006 | Marshall | C07K 14/525 435/69.1 |
| 2006/0136136 A1 | 6/2006 | Karpusas | |
| 2007/0015695 A1 | 1/2007 | Zhang et al. | |
| 2008/0254030 A1 | 10/2008 | Mackay | |
| 2009/0215071 A1 | 8/2009 | Cachero | |
| 2012/0201823 A1* | 8/2012 | Janatpour | C07K 16/2875 424/136.1 |
| 2014/0178329 A1* | 6/2014 | Pubul | C07K 14/525 424/85.1 |

FOREIGN PATENT DOCUMENTS

WO    WO-2004089982 A2 * 10/2004

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Tokuriki et al. Stability effects of mutations and protein evolvability. Curr Opin Structural Biol 19: 596-604, 2009.*
Chalk, M.B. Obesity: Addressing a multifactorial disease. The Case Manage 15(6): 47-49, 2004.*

(Continued)

*Primary Examiner* — Bridget E Bunner
(74) *Attorney, Agent, or Firm* — Calfee, Halter & Griswold LLP; Harry J. Guttman

(57) ABSTRACT

Provided herein are methods and compositions for modulating energy metabolism and weight in mammals, in particular by modulating thermogenesis associated with brown fat, including thermogenesis by brown fat or brown fat cells, adaptive thermogenesis by brown fat or brown fat cells, thermogenic capacity of brown fat or brown fat cells, or a combination thereof. More specifically, methods and compositions provided herein for treating or preventing obesity, or methods and compositions for identifying compounds effective for treating or preventing obesity are taught in connection with ligands such as B-cell activating factor (BAFF) and a proliferation-inducing ligand (APRIL), their receptors, and molecules that modulate the interactions between the ligands and receptors.

19 Claims, 9 Drawing Sheets

(56) References Cited

OTHER PUBLICATIONS

Palou et al. Obesity: molecular bases of a multifactorial problem. Eur J Nutr 39: 127-144, 2000.*
Lopez-Fraga et al. Biologically active APRIL is secreted following intracellular processing in the Golgi apparatus by furin convertase. EMBO Reports 2(10): 945-951, 2001.*
Yu et al. APRIL and TALL-1 and receptors BCMA and TACI: system for regulating humoral immunity. Nature Immunol 1(3): 252-256, 2000.*
Alexaki et al., "Adipocytes as Immune Cells: Differential Expression of TWEAK, BAFF, and APRIL and Their Receptors (Fn14, BAFF-R, TACI, and BCMA) at Different Stages of Normal and Pathological Adipose Tissue Development," The Journal of Immunology, vol. 183(9), p. 5948-5956, 2009.
Bossen, C., et al., "TACI, unlike BAFF-R, is solely activated by oligomeric BAFF and APRIL to support survival of activated B cells and plasma blasts," Blood, vol. 111(3), p. 1004-1012, 2008.
Cannon and Nedergaard, "Thyroid hormones: igniting brown fat via the brain," Nature Medicine, vol. 16, p. 965-967, 2010.
Cannon and Nedergaard, "Nonshivering thermogenesis and its adequate measurement in metabolic studies," The Journal of Experimental Biology, vol. 214, p. 242-253, 2011.
Collins, S., et al., "Positive and negative control of UCP1 gene transcription and the role of beta-adrenergic signaling networks," Int. J. Obes. (Lond.), vol. 34, Suppl. 1, p. S28-33, 2010.
Cypess, A.M., et al., "Identification and importance of brown adipose tissue in adult humans," New Eng. J Med., vol. 360, p. 1509-1517, 2009.
Divanovic, S., et al., "Inhibition of TLR-4/MD-2 signaling by RP105/MD-1," Journal of Endotoxin Research, vol. 11(6), p. 363-368, 2005.
Divanovic, S., et al., "Negative regulation of Toll-like receptor 4 signaling by the Toll-like receptor homolog RP105," Nature Immunology, vol. 6(6), p. 571-578, 2005.
Enerbäck S., "Human brown adipose tissue," Cell Metab., vol. 11, p. 248-252, 2010.
Groom, J.R., et al., "BAFF and MyD88 signals promote a lupuslike disease independent of T cells," J Exp. Med., vol. 204, p. 1959-1971, 2007.
Hofmann, S.M., et al., "Adipocyte LDL receptor-related protein-1 expression modulates postprandial lipid transport and glucose homeostasis in mice," J. Clin. Invest., vol. 117, p. 3271-3282, 2007.
Huard, B., et al., "BAFF production by antigen-presenting cells provides T cell co-stimulation," Int. Immunol., vol. 16, p. 467-475, 2004.
Kalled, S.L., "The role of BAFF in immune function and implications for autoimmunity," Immunol. Rev., vol. 204, p. 43-54, 2005.
Kim, Y.H., et al., "B cell activation factor (BAFF) is a novel adipokine that links obesity and inflammation," Exp. Mol. Med., vol. 41(3), p. 208-216, 2009.
Kirchner, H., et al., "GOAT links dietary lipids with the endocrine control of energy balance," Nat. Med., vol. 15, p. 741-745, 2009.
Kirchner, H., et al., "Ghrelin and PYY in the regulation of energy balance and metabolism: lessons from mouse mutants," Am. J. Physiol. Endocrinol. Metab., vol. 298, p. E909-919, 2010.
Kuroshima, A., "Brown adipose tissue thermogenesis as a physiological strategy for adaptation," Japan J. Physiol., vol. 43, p. 117, 1993.
Lammoglia, M.A., et al., "Effects of prepartum supplementary fat and muscle hypertrophy genotype on cold tolerance in newborn calves," Journal of Animal Science, vol. 77(8), p. 2227-2233, 1999.
Mackay, F. & Schneider, P., "Cracking the BAFF code," Nat. Rev. Immunol., vol. 9, p. 491-502, 2009.
Moon, E. and Park, H., "B cell activating factor (BAFF) gene promoter activity depends upon co-activator, p300," Immunobiology, vol. 212(8), p. 637-645, 2007.

Nedergaard and Cannon, "The Changed Metabolic World with Human Brown Adipose Tissue: Therapeutic Visions," Cell Metabolism, vol. 11(4), p. 268-272, 2010.
Pfluger, P.T., et al., "Simultaneous deletion of ghrelin and its receptor increases motor activity and energy expenditure," Am. J Physiol. Gastrointest. Liver Physiol., vol. 294, p. G610-618, 2008.
Pfluger, P.T., et al., "Sirt1 protects against high-fat diet-induced metabolic damage," Proc. Nat!. Acad. Sci., vol. 105, p. 9793-9798, 2008.
Schneider, P. & Tschopp, J., "BAFF and the regulation of B cell survival," Immunol. Lett., vol. 88, p. 57-62, 2003.
Shabalina, I. G., et al., "Uncoupling protein-1 is not leaky," Biochim. Biophys. Acta., vol. 1797, p. 773-784, 2010.
Skilling, H., et al., "Brown adipose tissue function in short-chain acyl-CoA dehydrogenase deficient mice," Biochem Biophys. Res. Commun., vol. 400(3), p. 318-322, 2010.
Stock and Rothwell, "Role of brown adipose tissue thermogenesis in overfeeding: a review," JR. Soc. Med., vol. 76(1), p. 71-73, 1983.
Thompson, J., et al., "BAFF-R, a newly identified TNF receptor that specifically interacts with BAFF," Science, vol. 293(5537), p. 2108-2111, 2001.
Tseng, Y.H., et al., "New role of bone morphogenetic protein 7 in brown adipogenesis and energy expenditure," Nature, vol. 454, p. 1000-1004, 2008.
Tseng, Y.H., et al., "Cellular bioenergetics as a target for obesity therapy," Nature Reviews Drug Discovery, vol. 9, p. 465-482, 2010.
Van Marken Lichtenbelt, et al., "Cold-activated brown adipose tissue in healthy men," New Eng. J Med., vol. 360, p. 1500-1507, 2009.
Virtanen, K.A., et al., "Functional brown adipose tissue in healthy adults," New Eng. J Med., vol. 360, p. 1518-1525, 2009.
Yuan, H. et al., "Characterization of the 5'-flanking region and regulation of transcription of human BAFF-R gene," DNA Cell Biol., vol. 29(3), p. 133-139, 2010.
Allen et al., "Cutting edge: regulation of TLR4-driven B cell proliferation by RP105 is not B cell autonomous," J. Immunol., Mar. 1, 2012, pp. 2065-2069, vol. 188(5).
Hariri et al., "High-fat diet-induced obesity in animal models," Nutrition Res. Rev., 2010, pp. 270-299, vol. 23.
Kawasaki et al., "Blockade of B-cell-activating factor signaling enhances hepatic steatosis induced by a high-fat diet and improves insulin sensitivity," Laboratory Invest., 2013, pp. 311-321, vol. 93.
Phillips, "The challenge of gene therapy and DNA delivery," J. Pharm. Pharmacol., 2001, pp. 1169-1174, vol. 53.
Rosini et al., "Diet-induced obesity, pp. rodent model for the study of obesity-related disorders," Rev. Assoc. Med. Bras., 2012, pp. 383-387, vol. 58(3).
Rubanyi, "The future of human gene therapy," Mol. Aspects Med., 2001, pp. 113-142, vol. 22.
Vincent et al., "The BAFF/APRIL System in SLE Pathogenesis" Nat. Rev. Rheumatol. (2014) vol. 10, pp. 365-373.
Cannon et al., "Brown Adipose Tissue: Function and Physiological Significance" Physiol Rev. (2004) vol. 84, pp. 277-359.
Chondronikola et al., "Brown Adipose Tissue Activation is Linked to Distinct Systemic Effects on Lipid Metabolism in Humans" Cell Metabolism (2016) vol. 23, pp. 1-7.
Dillon et al., "An APRIL to remember: novel TNF ligands as therapeutic targets" Nature Reviews/Drug Discovery (2006) vol. 5, pp. 235-246.
Nowak et al., "Evolution of genetic redundancy" Nature (1997) vol. 388, pp. 167-171.
Vincent et al., "The BAFF/APRIL system: Emerging functions beyond B cell biology and autoimmunity" Cytokine & Growth Factor Reviews (2013) vol. 24, pp. 203-215.
Wang et al., "Interferon regulatory factor 7 deficiency prevents diet-induced obesity and insulin resistance" Am J. Physiol Endocrinol. Metab (2013a) vol. 305, pp. E485-E495.
Wang et al., "Interferon regulatory factor 9 protects against hepatic insulin resistance and steatosis in male mice" Hepatology (2013b) vol. 58, No. 2, pp. 603-616.

* cited by examiner

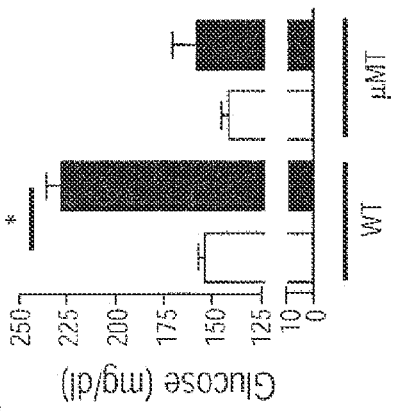
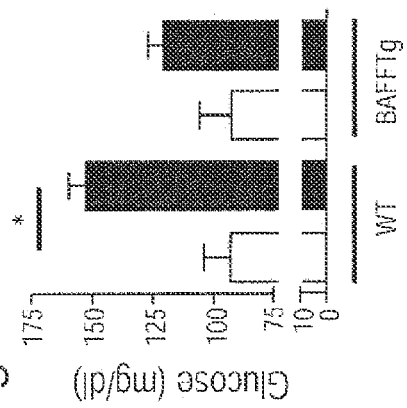
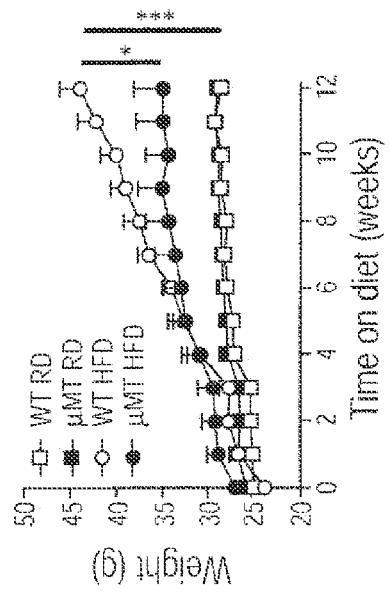
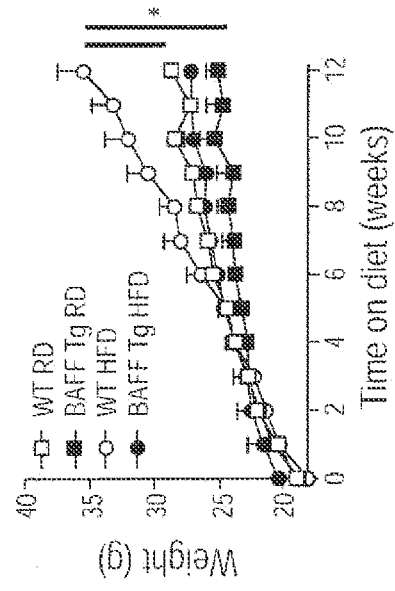

Figure 7A (SEQ ID NO.1: human BAFF, isoform 1, Accession No: Q9Y275)

```
  1  MDDSTEREQS  RLTSCLKKRE  EMKLKECVSI  LPRKESPSVR  SSKDGKLLAA  TLLLALLSCC
 61  LTVVSFYQVA  ALQGDLASLR  AELQGHHAEK  LPAGAGAPKA  GLEEAPAVTA  GLKIFEPPAP
121  GEGNSSQNSR  NKRAVQGPEE  TVTQDCLQLI  ADSETPTIQK  GSYTFVPWLL  SFKRGSALEE
181  KENKILVKET  GYFFIYGQVL  YTDKTYAMGH  LIQRKKVHVF  GDELSLVTLF  RCIQNMPETL
241  PNNSCYSAGI  AKLEEGDELQ  LAIPRENAQI  SLDGDVTFFG  ALKLL
```

Figure 7B (SEQ ID NO.2: human BAFF, isoform 2, Accession No: NP_001139117)

```
  1  MDDSTEREQS  RLTSCLKKRE  EMKLKECVSI  LPRKESPSVR  SSKDGKLLAA  TLLLALLSCC
 61  LTVVSFYQVA  ALQGDLASLR  AELQGHHAEK  LPAGAGAPKA  GLEEAPAVTA  GLKIFEPPAP
121  GEGNSSQNSR  NKRAVQGPEE  TGSYTFVPWL  LSFKRGSALE  EKENKILVKE  TGYFFIYGQV
181  LYTDKTYAMG  HLIQRKKVHV  FGDELSLVTL  FRCIQNMPET  LPNNSCYSAG  IAKLEEGDEL
241  QLAIPRENAQ  ISLDGDVTFF  GALKLL
```

Figure 7C (SEQ ID NO.3: murine BAFF, Accession No: NP_296371)

```
  1  MDESAKTLPP  PCLCFCSEKG  EDMKVGYDPI  TPQKEEGAWF  GICRDGRLLA  ATLLLALLSS
 61  SFTAMSLYQL  AALQADLMNL  RMELQSYRGS  ATPAAAGAPE  LTAGVKLLTP  AAPRPHNSSR
121  GHRNRRAFQG  PEETEQDVDL  SAPPAPCLPG  CRHSQHDDNG  MNLRNIIQDC  LQLIADSDTP
181  TIRKGTYTFV  PWLLSFKRGN  ALEEKENKIV  VRQTGYFFIV  SQVLYTDPIF  AMGHVIQRKK
241  VHVFGDEISL  VTLFRCIQNM  PKTLPNNSCY  SAGIARLEEG  DEIQLAIPRE  NAQISRNGDD
301  TFFGALKLL
```

Figure 7D (SEQ ID NO.4: human APRIL, Accession No: BAE16556)

```
  1 MPASSPFLLA PKGPPGNMGG PVREPALSVA LWLSWGAALG AVACAMALLT QQTELQSLRR
 61 EVSRLQGTGG PSQNCEGYPW QSLPEQSSDA LEAWENGERS RKRRAVLTQK QKKQHSVLHL
121 VPINATSKDD SDVTEVMWQP ALRRGRGLQA QGYGVRIQDA GVYLLYSQVL FQDVTFTMGQ
181 VVSREGQGRQ ETLFRCIRSM PSHPDRAYNS CYSAGVFHLH QGDILSVIIP RARAKLNLSP
241 HGTFLGFVKL
```

Figure 7E (SEQ ID NO.5: murine APRIL, Accession No: AAG22534)

```
  1 MPASSPGHMG GSVREPALSV ALWLSWGAVL GAVTCAVALL IQQTELQSLR REVSRLQRSG
 61 GPSQKQGERP WQSLWEQSPD VLEAWKDGAK SRRRRAVLTQ KHKKKHSVLH LVPVNITSKD
121 SDVTEVMWQP VLRRGRGLEA QGDIVRVWDT GIYLLYSQVL FHDVTFTMGQ VVSREGQGRR
181 ETLFRCIRSM PSDPDRAYNS CYSAGVFHLH QGDITVKIP RANAKLSLSP HGTFLGFVKL
```

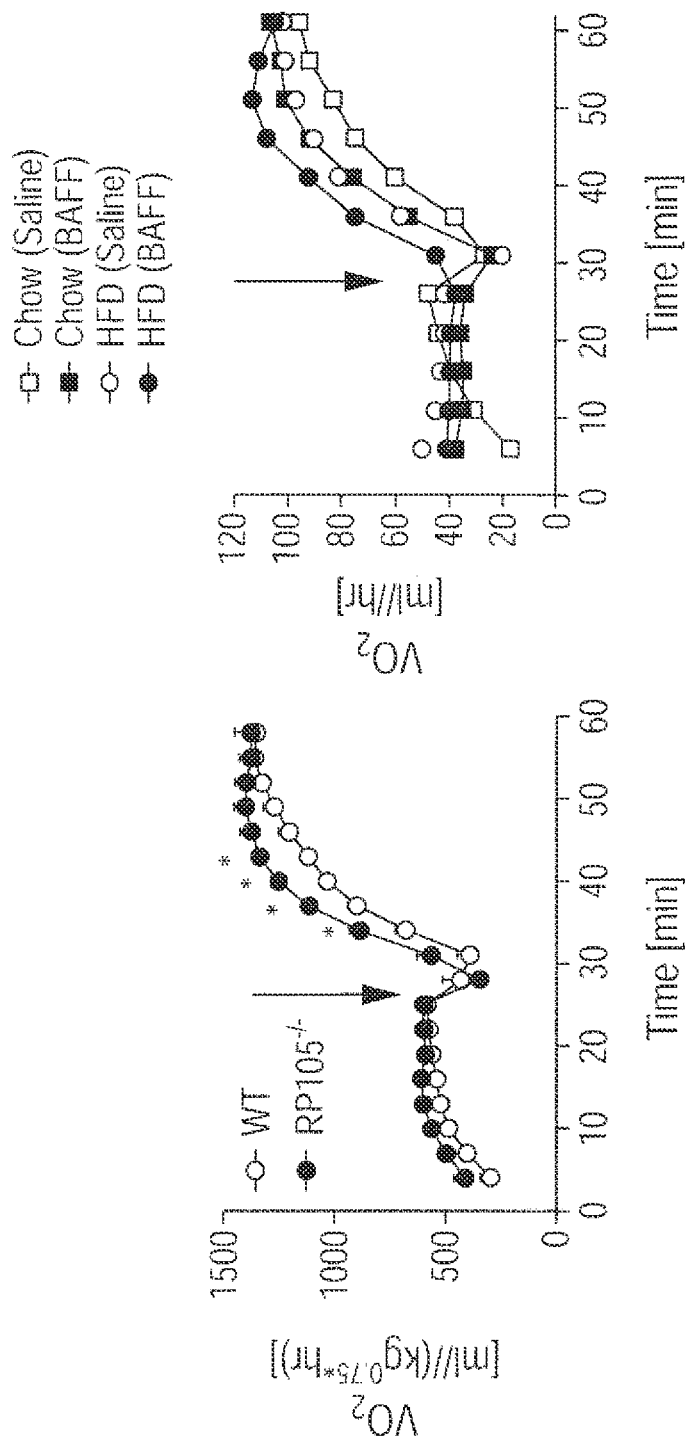

REGULATION OF ENERGY METABOLISM AND OBESITY BY MODULATING A PROLIFERATION-INDUCING LIGAND (APRIL) OR APRIL SIGNALING

CROSS REFERENCE TO RELATED APPLICATIONS

The present application is a divisional of and claims priority from U.S. Non-Provisional application Ser. No. 13/364,776, REGULATION OF ENERGY METABOLISM AND OBESITY BY MODULATING B CELL ACTIVATING FACTOR (BAFF, BLYS) OR BAFF SIGNALING, filed on Feb. 2, 2012, which is now U.S. Pat. No. 8,735,347 and which in turn claims the benefit of priority under 35 U.S.C. §119(e) to U.S. Provisional Application No. 61/438,964, REGULATION OF ENERGY METABOLISM AND OBESITY BY MODULATING B CELL ACTIVATING FACTOR (BAFF, BLYS) OR BAFF SIGNALING, filed on Feb. 2, 2011, both of which are incorporated by reference in their entirety.

STATEMENT REGARDING FEDERALLY-SPONSORED RESEARCH

This invention was made with government support under AI075159 awarded by the National Institutes of Health (NIH). The government has certain rights in the invention.

FIELD OF THE INVENTION

The invention disclosed herein generally relates to methods and compositions for modulating obesity in an animal, particularly a human. The invention disclosed herein generally further relates to methods and compositions for modulating the concentration and/or activity of B-cell activating factor (BAFF) or a proliferation-inducing ligand (APRIL), or their receptors or signaling partners. Methods and compositions for modulating factors upstream and downstream of BAFF and/or APRIL are also disclosed.

BACKGROUND

Obesity is a major risk factor for development of insulin resistance, dyslipidemia, hypertension (together: "metabolic syndrome"), type 2 diabetes, atherosclerosis, non-alcoholic fatty liver disease and diverse cancers. Obesity has become epidemic in Westernized cultures.

What is needed in the art are methods and compositions for identifying key factors in regulating obesity, particularly those associated with regulation of energy metabolism and weight gain/loss. More specifically, what is needed in the art are methods and compositions for treating or preventing obesity, or methods and compositions for identifying compounds effective for treating or preventing obesity.

SUMMARY OF THE INVENTION

Provided herein are methods and compositions for modulating energy metabolism and weight in mammals. More specifically, provided herein are methods and compositions for treating or preventing obesity, and methods and compositions for identifying compounds effective for treating or preventing obesity. Even more specifically, provided herein are methods and compositions for treating or preventing obesity, and methods and compositions for identifying compounds effective for preventing obesity taught in connection with B-cell activating factor (BAFF), its receptors, a proliferation-inducing ligand (APRIL), its receptors, and closely related molecules.

In one aspect, the present invention provides a method of treating or preventing obesity and/or one or more sequelae thereof in a subject. In particular, such methods comprise: administering to a subject in need of treatment or at risk for developing obesity and/or one or more sequelae thereof, a therapeutically effective amount of a pharmaceutical composition to enhance thermogenesis associated with brown fat or brown fat cells. In some embodiments, the pharmaceutical composition comprises, for example, a proliferation-inducing ligand (APRIL) that is recombinant or an agonistic variant thereof, a fragment of APRIL protein, an APRIL-based peptide or peptide analogue, an APRIL transcription regulator, a nucleic acid encoding at least partial sequence of APRIL, a second factor upstream or downstream from the interaction between APRIL and a second receptor, a regulator of a BAFF-first receptor interaction or an APRIL-second receptor interaction, or a combination thereof.

In some embodiments, thermogenesis associated with brown fat comprises thermogenesis by brown fat or brown fat cells, adaptive thermogenesis by brown fat or brown fat cells, thermogenic capacity of brown fat or brown fat cells, or a combination thereof.

In some embodiments, thermogenesis associated with brown fat or brown fat cells is further enhanced by increasing the level or activity of APRIL.

In some embodiments, the pharmaceutical composition is administered to a subject via parenteral, topical, oral, or local administration, injection, or a combination thereof.

In some embodiments, the subject is a human in need of treatment or at risk for developing obesity and/or one or more sequelae thereof.

In some embodiments, the method further comprises: identifying the subject (e.g. a human) in need of treatment or at risk for developing obesity and/or one or more sequelae thereof.

In some embodiments, the second receptor of APRIL is TACI or BCMA.

In some embodiments, thermogenesis associated with brown fat or brown fat cells is enhanced by increasing the level or activity of APRIL.

In some embodiments, thermogenesis associated with brown fat or brown fat cells is enhanced by increasing the level or activity of APRIL and BAFF.

In some embodiments, the pharmaceutical composition is a regulator of an APRIL-second receptor interaction selected from the group consisting of an APRIL-based peptide or an analogue thereof, an APRIL receptor analogue, and a co-activator of an APRIL-second receptor interaction.

In some embodiments, the first receptor and the second receptor are the same.

In some embodiments, the pharmaceutical composition is a recombinant APRIL, a fragment of APRIL, an APRIL agonistic variant, or a combination thereof.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A depicts mouse body weight. WT RD results are represented by white squares; WT HFD results are represented by white circles; RP105−/− RD results are represented by black squares; RP105−/− HFD results are represented by black circles. FIG. 1B depicts fasting glucose levels, quantified after 10 weeks on the diet. After an 8 hour fast, blood glucose levels were quantified by glucometer. RD results are represented by white bars; HFD results are represented by black bars. Data represent means+ SE in a single experiment, representative of 10 individual experiments; n=10-14 mice/group. For FIG. 1A, AUC ANOVA P<0.01, Tukey's correction ***P<0.001; for FIG. 1B, ANOVA P<0.0001, Tukey's correction *P<0.01.

FIG. 2A depicts a kinetic analysis of serum BAFF levels in WT and RP105−/− mice. Mice were mock-challenged or challenged with TLR4-specific E. coli lipopolysaccharide (LPS) (40 μg, i.p.), and serum BAFF levels were quantified kinetically. WT results are represented by white bars; RP105−/− results are represented by black bars. Data represent means+ SE in a single experiment; n=6 mice/group; unpaired, t test *P<0.05, P<0.005. FIG. 2B depicts baseline serum BAFF levels in RP105−/−, μMT, and BAFF-Tg mice. Data represent means+SE in a single experiment; n=3-4 mice/group; ANOVA P<0.0001, Tukey's correction *P<0.0001, on log transformed data.

FIGS. 3A-D illustrates that BAFF overexpression is associated with protection from weight gain and glucose dysmetabolism in diverse transgenic mice. Six to eight week-old male μMT, BAFF-transgenic, and WT mice (all on a C57BL/6 background) were placed on a HFD or RD. FIG. 3A depicts mouse body weight. WT RD results are represented by white squares; WT HFD results are represented by white circles; μMT RD results are represented by black squares; μMT HFD results are represented by black circles. FIG. 3B depicts fasting glucose levels, quantified after 9 weeks on the diet. RD results are represented by white bars; HFD results are represented by black bars. FIG. 3C depicts mouse body weight. WT RD results are represented by white squares; WT HFD results are represented by white circles; BAFF-transgenic RD results are represented by black squares; BAFF-transgenic FHD results are represented by black circles. FIG. 3D depicts fasting glucose levels, quantified after 12 weeks on the diet. RD results are represented by white bars; HFD results are represented by black bars. Data represent means+SE. FIGS. 3A-B data are taken from a single experiment, representative of 4 individual experiments; n=5-6 mice/group. FIGS. 3C-D data are taken from a single experiment; n=3-4 mice/group. For FIGS. 3A and 3C, AUC ANOVA P<0.01, Tukey's correction *P<0.05, ***P<0.001; for FIGS. 3B and 3D, ANOVA P<0.0001, Tukey's correction *P<0.01.

FIGS. 7A-E depict exemplary amino acid sequences of BAFF (SEQ ID NO 1-3) and exemplary amino acid sequences of APRIL (SEQ ID NO. 4 and NO. 5).

FIG. 8 illustrates an exemplary embodiment, demonstrating that adaptive thermogenesis was compared in RP105−/− and WT mice on a HFD. RP105−/− and WT mice, both on a C57BL/6 background, were placed on a HFD (60% kcal from fat, 20% kcal from carbohydrate, 20% kcal from protein, Research Diets #D12492i) for 14 days. Mice were anaesthetized by intraperitoneal injection of ketamine/xylazine, and the basal rate of oxygen consumption (at 33° C.) was quantified kinetically, at 3 minute intervals for 24 minutes, by indirect calorimetry. Oxygen consumption continued to be quantified kinetically after subsequent subcutaneous challenge, depicted on the figure with an arrow, with 1 mg/kg norepinephrine bitartrate. WT results are represented by open symbols; RP105−/− results are represented by closed symbols. Data represent means+/−SE of an n=4-5 mice/experimental group; t test; *P<0.05.

FIG. 9 illustrates an exemplary embodiment, demonstrating that WT C57BL/6 mice were placed on either a HFD (60% kcal from fat, 20% kcal from carbohydrate, 20% kcal from protein, Research Diets #D12492i) or an RD (chow; 13.5% kcal from fat, 59% kcal from carbohydrate, 27.5% kcal from protein, Lab Diet #5010) for 14 days. Mice were subsequently given 1 mg/kg recombinant BAFF or vehicle control (saline) by intraperitoneal injection 18 hours and 2 hours prior to quantification of oxygen consumption. Mice were then anaesthetized by intraperitoneal injection of ketamine/xylazine, and the basal rate of oxygen consumption (at 330° C.) was quantified kinetically, at 5 minute intervals for 25 minutes, by indirect calorimetry. Oxygen consumption continued to be quantified kinetically after subsequent subcutaneous challenge, depicted on the figure with an arrow, with 1 mg/kg norepinephrine bitartrate. RD+saline results are represented by open squares; RD+BAFF results are represented by closed squares; HFD+saline results are represented by open circles; HFD+BAFF results are represented by closed circles. Data represent single mice/experimental group.

DETAILED DESCRIPTION OF THE INVENTION

Definitions

Unless otherwise noted, terms are to be understood according to conventional usage by those of ordinary skill in the relevant art.

As used herein, the term "pharmaceutical composition" encompasses any protein, peptide, peptide analogue, nucleic acid, or small molecule that can interfere with thermogenesis by brown fat. In particular, those compositions that can interfere with signaling pathways mediated by B-cell activating factor (BAFF) and/or a proliferation-inducing ligand (APRIL).

Obesity and RP105

Figure 1A:
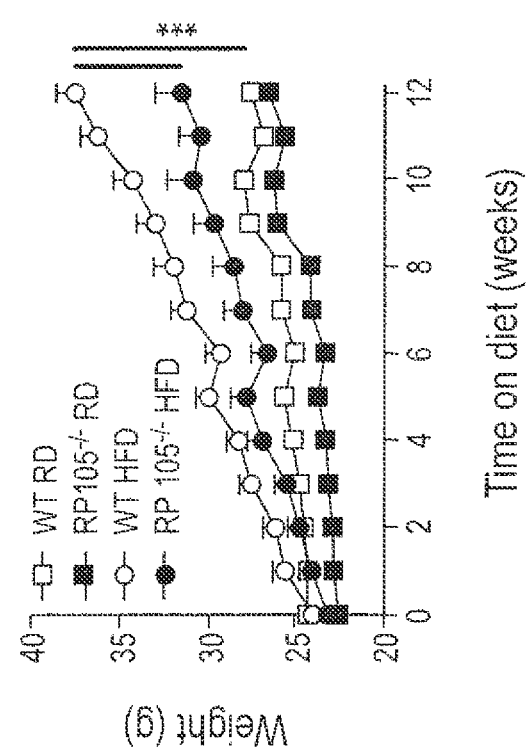
FIGS. 1A-B illustrates that RP105-deficient mice are protected from obesity and glucose dysmetabolism. Six to eight week-old male C57BL/6 RP105−/− mice and wild type (WT) controls were placed on a high fat diet (HFD) or a regular chow diet (RD).

Radioprotective protein 105 kDa (RP105) is an endogenous modulator of Toll-like receptor (TLR) signaling pathways. Originally described as a B cell-specific molecule that drives proliferation when cross-linked by antibodies, it has been shown that: (a) RP105 expression mirrors that of TLRs on myeloid and other cells; and (b) RP105 inhibits TLR4 signaling in primary myeloid cells and cell lines and regulates in vivo responses to lipopolysaccharide (LPS). The data indicate that RP105 also regulates energy metabolism in response to caloric excess. As shown in FIG. 1A, RP105-deficient mice gain significantly less weight than wild type (WT) controls when subjected to stress induced by a high fat diet (HFD). RP105−/− mice eat the same amount as WT controls on a HFD and have identical food absorption (as quantified by bomb calorimetry). These data indicate that RP105 regulates metabolic efficiency in response to caloric excess, hence indicating that RP105 regulates energy metabolism. Adaptive thermogenesis by brown fat, which occurs in response to caloric excess as well as cold stress, is dependent on the expression of uncoupling protein 1 (UCP1). The data also indicate that: (a) brown fat from RP105−/− mice on a HFD express significantly more UCP1 mRNA than WT controls (data not shown); and (b) brown fat mitochondria from RP105−/− mice on a HFD exhibit significantly higher degree of uncoupled respiration than brown fat mitochondria from wild type controls on a HFD.

Additional information on RP105 can be found, for example, in Divanovic et al., 2005, "Inhibition of TLR-4/MD-2 signaling by RP105/MD-1," *Journal of Endotoxin Research* 11(6):363-368; Divanovic et al., 2005, "Negative regulation of Toll-like receptor 4 signaling by the Toll-like receptor homolog RP105," *Nature Immunology* 6(6):571-578, each of which is hereby incorporated by references herein in its entirety.

Thermogenesis by Brown Fat

In one aspect, BAFF modulates energy metabolism and metabolic efficiency by modulating thermogenesis by brown adipose tissue (BAT, or brown fat). More specifically, regulation of thermogenesis by brown fat includes but is not limited to thermogenesis, adaptive thermogenesis and thermogenic capacity by brown fat. Thermogenesis is the process of heat production in organisms. While thermogenesis occurs in all cells and organisms; brown fat-associated thermogenesis occurs in mammals.

In some embodiments, thermogenesis encompasses those processes initiated through locomotion and intentional movement of the muscles, including but not limited to exercise-associated thermogenesis (EAT), non-exercise activity thermogenesis (NEAT), and diet-induced thermogenesis (DIT).

In some embodiments, thermogenesis encompasses various types of adaptive thermogenesis caused, for example, by changes in the surrounding temperature of the animal or changes in dietary intake.

In an animal, heat can be generated by the conversion of the chemical energy of ATP into kinetic energy, i.e. by shivering. Non-shivering thermogenesis occurs in the brown fat that is present in most if not all mammals, including humans. In this process, substances such as free fatty acids (derived from triacylglycerols) inhibit thermogenin (uncoupling protein-1 or UCP1) by removing purine (in the form of ADP, GDP and others), which causes an influx of H$^+$ into the matrix of the mitochondria and bypasses the ATP synthase channel. This uncouples oxidative phosphorylation, and the energy from the proton motive force is dissipated as heat rather than producing ATP from ADP, which would store chemical energy for the body's use. Thermogenesis can also be produced by leakage of the sodium-potassium pump and the Ca$^{2+}$ pump. Thermogenesis is contributed to by futile cycles, such as the simultaneous occurrence of lipogenesis and lipolysis or glycolysis and gluconeogenesis.

Regulation of non-shivering, adaptive thermogenesis by brown fat is regulated by the adrenergic stimulation by the sympathetic nervous system, as well as by the central nervous system activities of thyroxine and leptin; the latter hormones stimulate thermogenesis by activating the sympathetic nervous system. See, for example, Cannon and Nedergaard, 2010, "Thyroid hormones: igniting brown fat via the brain," *Nature Medicine* 16:965-967, which is hereby incorporated by reference herein in its entirety. In some embodiments, the level of any or a combination of these indicators are used to monitor thermogenesis. For example, upregulation of the thermogenic response of mice to norepinephrine challenge is a standard experimental test for the evaluation of adaptive thermogenesis. Alternatively, cold exposure can be used to induce and measure adaptive thermogenic capacity. See, for example, Skilling et al., 2010, "Brown adipose tissue function in short-chain acyl-CoA dehydrogenase deficient mice," *Biochem Biophys. Res. Commun.* 400(3):318-322; Lammoglia et al., 2010, "Effects of prepartum supplementary fat and muscle hypertrophy genotype on cold tolerance in newborn calves," *Journal of Animal Science* 77(8):2227-2233, each of which is hereby incorporated by reference herein in its entirety.

An overview of the role of brown fat in adaptive thermogenesis can be found, for example, in Stock and Rothwell, 1983, "Role of brown adipose tissue thermogenesis in overfeeding: a review," *J. R. Soc. Med.* 76(1):71-73, which is hereby incorporated by reference herein in its entirety. Additional information can be found, for example, in Nedergaard and Cannon, 2010, "The Changed Metabolic World with Human Brown Adipose Tissue: Therapeutic Visions," *Cell Metabolism* 11(4):268-272; Cannon and Nedergaard, 2011, "Nonshivering thermogenesis and its adequate measurement in metabolic studies," *The Journal of Experimental Biology* 214: 242-253, each of which is hereby incorporated by reference herein in its entirety.

In accordance with the present invention, any compositions and/or means, which alter thermogenesis, e.g. thermogensis by brown fat, in an animal can affect the weight status of the animal. The animal can be a human, a cow, a horse, a sheep, a dog, a mouse, etc. In particular, any compositions and/or means which can upregulate thermogenesis by brown fat (or brown fat cells), adaptive thermogenesis by brown fat (or brown fat cells), and/or the thermogenic capacity of brown fat cells (or brown fat cells), can be used to prevent or treat obesity. Similarly, any compositions and/or means, which can downregulate thermogenesis by brown fat (or brown fat cells), adaptive thermogenesis by brown fat (or brown fat cells), and/or the thermogenic capacity of brown fat cells (or brown fat cells), can be used to prevent or treat excessive weight loss (such as anorexia).

In some embodiments, modulation of thermogenesis is achieved by modifying the function of brown adipocytes or brown adipose tissue.

Brown fat is one of two types of fat or adipose tissue found in mammals (the other being white adipose tissue). Brown fat is present in most if not all mammals, including humans, and is especially abundant in newborns and in hibernating mammals. BAFF and various homologues can be found in various mammals as well. Given the prevalence of BAFF and brown fat in different mammals and their important role in regulating thermogenesis, compositions and/or methods targeting BAFF-mediated thermogenesis by brown fat can serve as therapeutic options for diseases such as obesity and sequelae thereof.

Adaptive thermogenesis is defined as the regulated production of heat caused by uncoupled respiration in brown fat, resulting in metabolic inefficiency and is believed to be a mechanism for modulating cold stress and dietary excess. In contrast to white adipocytes (white fat cells), which contain a single lipid droplet, brown adipocytes contain numerous smaller droplets and a much higher number of mitochondria, which contain iron and account for the brown color. Brown fat also contains more capillaries than white fat, since it has a greater need for oxygen than most tissues.

BAT is a unique form of fat that is found in varying amounts throughout the mammalian genus. Bears, rodents, and other hibernating animals that live in cold weather have an abundance of this specialized fat. Humans have small deposits throughout the body, although the content is much higher during infancy. BAT cells are smaller than normal storage cells, contain less fat, and are laden with mitochondria. These mitochondria hold a specialized uncoupling protein, namely uncoupling protein 1 (UCP1, also known as thermogenin), that allows for uncoupling of oxidative phosphorylation, leading to the production of heat but no ATP.

The adaptive thermogenic capacity of brown adipose tissue is induced through two primary mechanisms, cold environment and excess food consumption. These stimuli drive the differentiation, proliferation, and function of brown fat adipocytes.

Thermogenesis by brown fat is, with basal metabolic rate and activity-induced thermogenesis, one of the three components of daily energy expenditure. Thermogenesis by brown fat is thought to play a role in the prevention or control of obesity. Additional details can be found, for example, in Nedergaard and Cannon, 2010, "The changed metabolic world with human brown adipose tissue: therapeutic visions," *Cell Metab.* 11:268-272; Enerback S. 2010, "Human brown adipose tissue," *Cell Metab.* 11:248-252; and Tseng et al., 2010, "Cellular bioenergetics as a target for obesity therapy," *Nature Reviews Drug Discovery* 9:465-482, each of which is hereby incorporated by reference herein in its entirety.

The mitochondria in a eukaryotic cell utilize fuels to produce energy (in the form of ATP). This process involves storing energy as a proton gradient, also known as the proton motive force (PMF), across the mitochondrial inner membrane. This energy is used to synthesize ATP when the protons flow across the membrane (down their concentration gradient) through the ATP synthase enzyme; this is known as chemiosmosis. In warm-blooded animals, body heat is maintained in part by signaling the mitochondria to allow protons to run back along the gradient without producing ATP. This can occur since an alternative return route for the protons exists through UCP1 in the inner membrane, which facilitates the return of the protons after they have been actively pumped out of the mitochondria by the electron transport chain. This alternative route for protons uncouples oxidative phosphorylation, and the energy in the PMF is instead released as heat.

To some degree, all cells give off heat. However, brown adipose tissue is highly specialized for thermogenesis through uncoupled respiration. This is because each cell has a higher number of mitochondria compared to more typical cells. In addition, these mitochondria contain UCP-1.

More details about the connection between brown fat and thermogenesis in humans can be found, for example, in Cypess et al., 2009, "Identification and importance of brown adipose tissue in adult humans," *New Eng. J. Med.* 360: 1509-1517; Kuroshima 1993, "Brown adipose tissue thermogenesis as a physiological strategy for adaptation," *Japan J. Physiol.* 43:117; van Marken Lichtenbelt et al., 2009, "Cold-activated brown adipose tissue in healthy men," *New Eng. J. Med.* 360:1500-1507; Virtanen et al., 2009, "Functional brown adipose tissue in healthy adults," *New Eng. J. Med.* 360:1518-1525, each of which is hereby incorporated by reference herein in its entirety.

In some embodiments, recruitment of adaptive thermogenic capacity and adaptive thermogenesis by brown fat occurs in response to changes in dietary intake, including diet with caloric excess and diets that are calorie rich but are limiting in essential nutrients.

Diet-induced-thermogenesis (DIT) has two essential components which contribute to energy expenditure. Immediately after eating and for a period of several hours thereafter, the body expends more energy to support the ingestion, digestion, and absorption of nutrients. In addition, the body produces heat in brown adipose tissue (BAT) due to increased sympathetic nervous system activity. The latter is adaptive thermogenesis mediated by brown fat or brown fat cells.

Thus, in some embodiments, treatment of obesity can be a combinatorial approach. That is to say, additional compositions and methods can be used in addition to those used for modulating BAFF-mediated thermogenesis by brown fat.

In some embodiments, compositions and methods disclosed herein can be applied to the context of regulating diet-related thermogenesis by brown fat.

In some embodiments, altering the expression of specific molecules associated with thermogenesis by brown fat can modify energy metabolism and/or control weight gain.

Additional information on energy metabolism (e.g. thermogenesis) and its association with brown fat can be found, for example, in Tseng, Y. H., et al., 2008, "New role of bone morphogenetic protein 7 in brown adipogenesis and energy expenditure," *Nature* 454:1000-1004; Pfluger, P. T., et al., 2008, "Sirt1 protects against high-fat diet-induced metabolic damage," *Proc. Natl. Acad. Sci. U.S.A.* 105:9793-9798; Hofmann, S. M., et al., 2007, "Adipocyte LDL receptor-related protein-1 expression modulates postprandial lipid transport and glucose homeostasis in mice," *J. Clin. Invest.* 117:3271-3282; Kirchner, H., et al., 2010, "Ghrelin and PYY in the regulation of energy balance and metabolism: lessons from mouse mutants," *Am. J. Physiol. Endocrinol. Metab.* 298:E909-919; Pfluger, P. T., et al., 2008, "Simultaneous deletion of ghrelin and its receptor increases motor activity and energy expenditure," *Am. J. Physiol. Gastrointest. Liver Physiol.* 294:G610-618; Kirchner, H., et al., 2009, "GOAT links dietary lipids with the endocrine control of energy balance," *Nat. Med.* 15:741-745; Collins, S., et al., 2010, "Positive and negative control of UCP1 gene transcription and the role of beta-adrenergic signaling networks," *Int. J. Obes.* (*Lond.*) 34 Suppl 1:S28-33; Shabalina, I. G., et al., 2010, "Uncoupling protein-1 is not leaky," *Biochim. Biophys. Acta* 1797:773-784, each of which is hereby incorporated by reference herein in its entirety.

B-Cell Activating Factor (BAFF)

Provided herein are compositions and/or methods for enhancing thermogenesis by modulating cell-signaling pathways relating to thermogenesis by brown fat, for example, the BAFF signaling pathway and the like. BAFF, also known as tumor necrosis factor (TNF) ligand superfamily member 13B is a protein that in humans is encoded by the TNFLSF13B gene. BAFF is also known as B lymphocyte stimulator (BLyS) and TNF- and APOL-related leukocyte expressed ligand (TALL-1), THANK, zTNF4, and the dendritic cell-derived TNF-like molecule (CD257 antigen; cluster of differentiation 257). BAFF is a type II transmembrane protein that can be proteolytically cleaved between Arg 133 and Ala 134 and released as a soluble protein.

BAFF is a cytokine that belongs to the TNF ligand family and is a ligand for receptors TNFRSF13B/TACI (cytophilin ligand interactor), TNFRSF17/BCMA (B-cell maturation antigen), and TNFRSF13C/BAFF-R (BAFF-receptor). This cytokine acts as a potent B-cell activator. It has been also shown to play an important role in the proliferation and differentiation of B-cells.

Human BAFF is a 285 amino acid (AA) peptide consisting of a 218 AA acid extracellular domain, a 21 AA transmembrane region, and a 46 AA cytoplasmic tail. BAFF is a glycoprotein, which undergoes glycosylation at residue 124. It is expressed as a transmembrane protein on various cell types, including monocytes, dendritic cells, B-cells, adipocytes, and bone marrow stromal cells. The transmembrane form can be cleaved from the membrane to generate a soluble protein fragment. BAFF is the natural ligand of three TNF receptors, namely BAFF-R, TACI, and BCMA, all of which are type III transmembrane proteins and have differing binding affinities for BAFF. These receptors are expressed mainly on mature B lymphocytes. TACI is also found on a subset of T-cells and BCMA on plasma cells.

Receptors of BAFF and other related ligands in parallel signaling pathways can be found in a variety of cell/tissue type, including adipocytes. Additional examples of receptors can be found, for example, in Alexaki et al., 2009, "Adipocytes as Immune Cells: Differential Expression of TWEAK, BAFF, and APRIL and Their Receptors (Fn14, BAFF-R, TACI, and BCMA) at Different Stages of Normal and Pathological Adipose Tissue Development," *The Journal of Immunology* 183(9):5948-5956; Kim et al., 2009, "B cell activation factor (BAFF) is a novel adipokine that links obesity and inflammation," *Exp. Mol. Med.* 41(3):208-216, each of which is hereby incorporated by reference herein in its entirety.

TACI also binds to APRIL, which is a protein similar to BAFF. BCMA displays an intermediate binding phenotype and will work with either BAFF or APRIL to varying degrees. Signaling through BAFF-R and BCMA stimulates B lymphocytes to undergo proliferation and to counter apoptosis. Signaling is also achieved through TACI. BAFF is expressed by myeloid cells and by unidentified radiation-resistant cells, possibly stromal cells of secondary lymphoid organs. BAFF is either expressed at the cell surface or released into a soluble form through cleavage by an uncharacterized furin. Members of the TNF family usually assemble as trimers, but soluble BAFF was crystallized both as a trimer (e.g. a homotrimer) and as a virus-like structure resulting from the ordered assembly of 20 trimers through an unusually long loop of BAFF between beta-sheets D and E (DE loop). Recent work has shown that a BAFF 60-mer is also produced by cells expressing BAFF endogenously and that the 60-mer was moderately more potent than the 3-mer at costimulating BCR-induced thymidine uptake in primary B-cells. APRIL, a close homolog of BAFF, can also co-stimulate B-cells but requires oligomerization to do so. For example, APRIL functions as a homotrimer, The state of oligomerization can be another level of regulation. For example, it has been shown that, in contrast to BAFF-R, TACI was unresponsive to the BAFF 3-mer yet provided the survival and differentiation signals when triggered by oligomeric forms of BAFF or APRIL. BAFF 60-mer is one form of oligomeric BAFF that can activate TACI and that exists naturally in vivo.

A strong pH dependence of oligomerization state has been observed: at pH 6.0 BAFF was 100% trimeric and at pH 7.4 100% 60-mer. Thus, it possible to manipulate pH value anywhere between 6.0 and 7.4 in order to achieve the desired levels of trimer and 60-mer. In some embodiments, recombinant BAFF is genetically modified in order to preferentially form the trimer or 60-mer. Methods for making BAFF trimers and BAFF 60-mers can be found, for example, in United States Patent Publication No. 20090215071 to Cachero et al.; U.S. Pat. No. 7,553,930, each of which is hereby incorporated by reference herein in its entirety.

The role of BAFF in energy metabolism and control of weight can be found in Examples 3-6. In particular, Example 3 (FIGS. 1-4) illustrates that BAFF overexpression is associated with protection from weight gain and glucose dysmetabolism. The correlation between BAFF overexpression and weight gain can be observed across mice of different genotypes (Example 4). Modifications of BAFF, either its level of expression or activity, are provided as methods for treating disorders in energy metabolism (e.g. obesity).

The present invention provides that increased BAFF in vivo is associated with protection from obesity. In particular, the protection is associated with increased UCP-1 expression and increased uncoupled respiration in brown fat mitochondria. It has been demonstrated in vitro that BAFF directly increases brown adipocyte respiration. More specifically, the presence of BAFF stimulates brown adipocyte respiration in vitro. Example 5 shows that level of BAFF correlates with level of oxygen consumption rate. Example 6 further illustrates that the enhanced respiration level of brown fat cells (e.g. resulting from stress induced by a HFD) corresponds with increased uncoupled respiration in brown fat mitochondria. Example 9 further demonstrates that BAFF treatment up-regulates norepinephrine-induced thermogenesis in vivo. Thus, BAFF drives increased thermogenesis, thermogenic capacity, and/or adapative thermogenesis by brown fat.

Additional information on BAFF, its homologues and receptors, and their functions can be found, for example, in Schneider, P. & Tschopp, J., 2003, "BAFF and the regulation of B cell survival," *Immunol. Lett.* 88:57-62; Groom, J. R., et al., 2007, "BAFF and MyD88 signals promote a lupuslike disease independent of T cells," *J. Exp. Med.* 204:1959-1971; Kalled, S. L., 2005, "The role of BAFF in immune function and implications for autoimmunity," *Immunol. Rev.* 204:43-54; Mackay, F. & Schneider, P., 2009, "Cracking the BAFF code," *Nat. Rev. Immunol.* 9:491-502; Kim, Y. H., 2009, "B cell activation factor (BAFF) is a novel adipokine that links obesity and inflammation," *Exp. Mol. Med.* 41:208-216; Alexaki, V. I., et al., 2009, "Adipocytes as immune cells: differential expression of TWEAK, BAFF, and APRIL and their receptors (Fn14, BAFF-R, TACI, and BCMA) at different stages of normal and pathological adipose tissue development," *J. Immunol.* 183:5948-5956; Bossen, C., et al., 2008, "TACI, unlike BAFF-R, is solely activated by oligomeric BAFF and APRIL to support survival of activated B cells and plasmablasts," *Blood* 111(3): 1004-1012; Huard, B., et al., 2004, "BAFF production by antigen-presenting cells provides T cell co-stimulation," *Int. Immunol.* 16:467-475, each of which is hereby incorporated by reference herein in its entirety.

BAFF, Receptors, and Applications Thereof

Any methods or compositions that can modulate the level and/or activity of BAFF can be used to modulate energy metabolism, in particular thermogenesis by brown fat. More precisely, any methods or compositions that can modulate the level and/or activity of BAFF can be used to enhance thermogenesis by brown fat, thereby achieving weight control. Any such methods and/or compositions can be used to treat and/or prevent obesity.

Given BAFF and related signaling pathways and their importance in metabolism regulation and thermogenesis, the methods and/or compositions described herein are applied directly to enhance the level and/or activity of BAFF. For example, BAFF can be overexpressed in the targeted animal through genetic modification (Examples 3 and 4) and can be used to treat and prevent obesity.

BAFF is believed to bind its receptors as oligomers, for example, as heterotrimers, homotrimers, or 60-mers. BAFF of any form can be used in the present invention.

Recombinant human BAFF is commercially available, for example, from R&D Systems, Inc. (Minneapolis, Minn.). In some embodiments, recombinant BAFF is treated with an appropriate buffer before intraperitoneal delivery. For example, mildly acidic conditions favor formation of the trimer (e.g. around pH 6.0), while nearly neutral pH conditions (e.g. around pH 7.0) favor oligomerization and produce the 60-mer presumably by duplicating trimers. It possible to use a delivery buffer with a pH value anywhere between 6.0 and 7.4 in order to achieve the formation of the desired trimer and 60-mer composition. In some embodiments, recombinant BAFF is genetically modified in order to preferentially select for the trimer or 60-mer. Methods for making BAFF trimers and BAFF 60-mers can be found, for example, in United States Patent Publication No. 20090215071 to Cachero et al.; U.S. Pat. No. 7,553,930, each of which is hereby incorporated by reference herein in its entirety.

In some embodiments, variants of BAFF are used in treating and preventing obesity. For example, a shortened version of recombinant human BAFF of only 153 amino acids is also available as a lyophilized protein from BioVision (Mountain View, Calif.). Additional BAFF variants that can be used to treat obesity also include those disclosed in U.S. Pat. No. 7,553,930 to Desjarlais et al., United States Patent Publication No. 20060136136 by Karpusas, each of which is hereby incorporated by reference herein in its entirety.

In some embodiments, antibodies to membrane-bound BAFF are used because they can drive signaling. In some embodiments, other agonists of BAFF are used to enhance signaling. Exemplary BAFF agonists include but are not limited to: (a) a soluble BAFF polypeptide, (b) an agonist anti-BAFF antibody or antigen-binding fragment thereof, and (c) an agonist anti-BR3 antibody or antigen-binding fragment thereof. Examples of soluble BAFF peptides include but are not limited to BAFF amino acids 145-284, amino acids 169-308, and amino acids 11-150.

In some embodiments, analogues of soluble BAFF peptides are used in treating and preventing obesity. For example, a peptide analogues comprises a sequence that is at least 50% or more, 60% or more, 70% or more, 80% or more, 90% or more, or 95% or more of any of the soluble BAFF peptide sequences. These analogues can bear 50% or more, 60% or more, 70% or more, 80% or more, 90% or more, or 95% or more sequence homology to those soluble fragments of BAFF. In turn, the soluble fragments of BAFF can be 5% or more, 10% or more, 20% or more, 30% or more, 40% or more, 50% or more, 60% or more, 70% or more, 80% or more, 90% or more, or 95% or more of the full length of the BAFF protein. FIGS. 7A-C depict exemplary amino acid sequences of BAFF (SEQ ID NOs 1-3).

Additional examples of BAFF agonists can be found, for example, in United States Patent Publication No. 20080254030 by Mackay et al., which is hereby incorporated by reference herein in its entirety.

In some embodiments, overexpression of BAFF is achieved by genetic manipulation, as described in Examples 3 and 4. In some embodiments, transcription regulators are used. For example, BAFF transcript expression increases by a toll-like receptor 4 (TLR4) agonist, a lipopolysaccharide (LPS), reactive oxygen species (ROS) production, NF-κB activation, p65, and co-activator, p300.

In some embodiments, molecules that affect the activities of these BAFF transcription regulators can be used to modulate the expression level of BAFF. See, for example, Moon, E. and Park, H., 2007, "B cell activating factor (BAFF) gene promoter activity depends upon co-activator, p300," *Immunobiology* 212(8):637-645, which is hereby incorporated by reference herein in its entirety.

In some embodiments, recombinant BAFF can be introduced into a target animal by either gene delivery or protein delivery. For example, a vector encoding BAFF can be introduced into a target animal followed by induction of its expression with specification compounds.

It will be understood by one of skill in the art that overexpressing BAFF may also lead to adverse side effects beside the desired protection against weight gain. For example, BAFF has been implicated in autoimmune diseases. However, the levels of BAFF required for triggering autoimmune disease are much higher than those required for modulating a thermogenic response and/or modulating weight.

In some embodiments, the methods and/or compositions are applied indirectly to BAFF, though an upstream or downstream effector of BAFF. For example, an inhibitor of BAFF can be removed permanently (e.g. via genetic knock-out), temporarily curtailed (e.g. by using RNAi agents targeting the BAFF inhibitor to cause temporary reduced expression, or by using small molecule compounds that bind to the BAFF inhibitor to achieve the same effects).

In some embodiments, modulation of BAFF activity is performed by modulating any of the factors that interact with BAFF, including but are not limited to BAFF-R, TACI, BCMA, and APRIL, a relative of BAFF which competes with BAFF in binding to TACI and BCMA. BAFF's functional role in energy metabolism and weight control is believed to have been achieved through one or more pathways involving these receptors.

BAFF-R, or tumor necrosis factor receptor superfamily member 13C (TNFRSF13), is a protein that in humans is encoded by the TNFRSF13C gene, which interacts with BAFF. BAFF enhances B-cell survival in vitro and is a regulator of the peripheral B-cell population. Overexpression of BAFF in mice results in mature B-cell hyperplasia and symptoms of systemic lupus erythematosus (SLE). Also, some SLE patients have increased levels of BAFF in serum. Therefore, it has been proposed that abnormally high levels of BAFF may contribute to the pathogenesis of autoimmune diseases by enhancing the survival of autoreactive B-cells. The protein encoded by this gene is a receptor for BAFF and is a type III transmembrane protein containing a single extracellular phenylalanine-rich domain. It is thought that this receptor is the principal receptor required for BAFF-mediated mature B-cell survival. More details on BAFF-R can be found in Thompson, J. et al., 2001, "BAFF-R, a newly identified TNF receptor that specifically interacts with BAFF," *Science* 293(5537):2108-2111; U.S. Pat. No. 7,635,677 to Ambrose et al., each of which is hereby incorporated by reference herein in its entirety.

TACI, also known as tumor necrosis factor receptor superfamily member 13B (TNFRSF13B), is a transmembrane receptor protein found predominantly on the surface of B cells, which are an important part of the immune system. TACI is a lymphocyte-specific member of the TNF receptor superfamily. It was originally discovered due to its ability to interact with calcium-modulator and cyclophilin ligand (CAML). TACI was later found to play a crucial role in humoral immunity by interacting with two members of the TNF family, namely BAFF and APRIL. These proteins signal through TACI, inducing activation of several transcription factors, including NFAT, AP-1, and NF-κB, which then modulate cellular activities. Defects in the function of TACI can lead to immune system diseases.

In some embodiments, a pharmaceutical composition comprising oligomeric forms of BAFF and APRIL can be used to activate TACI-based signaling. This is due to the activation of TACI-based signaling by oligomeric forms of BAFF and APRIL.

BCMA, or tumor necrosis factor receptor superfamily member 17, is a protein that in humans is encoded by the TNFRSF17 gene. BCMA is a member of the TNF-receptor superfamily. This receptor is preferentially expressed in mature B lymphocytes, and may be important for B-cell development and autoimmune response. This receptor has been shown to specifically bind to the TNF (ligand) superfamily, member 13b (TNFSF13B/TALL-1/BAFF), and to lead to NF-κB and MAPK8/JNK activation. This receptor also binds to various TRAF family members and thus can transduce signals for cell survival and proliferation.

APRIL is another TNF-like cytokine that stimulates tumor cell growth. Within the TNF ligand superfamily, APRIL is most similar to B-cell activation factor (BAFF), with which it shares 30% sequence identity. APRIL binds the B-cell maturation antigen (BCMA) and TACI receptors with high affinity; both of these receptors have also been shown to bind BAFF, although BCMA has significantly higher affinity for APRIL than BAFF.

In some embodiments, cell-signaling pathways parallel to the BAFF pathway, such as the APRIL pathway, are targeted for treating and preventing obesity. APRIL signaling can be synergistic to the effect of BAFF signaling. Similarly, any methods and/or composition designs applicable to BAFF can be used in formulating any composition based on APRIL. For example, recombinant APRIL and variants thereof can be delivered directly to a subject. Additionally soluble fragments of APRIL and analogues thereof can also be used in the present invention. These analogous can bear 50% or more, 60% or more, 70% or more, 80% or more, 90% or more, or 95% or more sequence homology to those soluble fragments of APRIL. In turn, the soluble fragments of APRIL can be 5% or more, 10% or more, 20% or more, 30% or more, 40% or more, 50% or more, 60% or more, 70% or more, 80% or more, 90% or more, or 95% or more of the full length of the APRIL protein. FIGS. 7D-E depict exemplary amino acid sequences of APRIL (SEQ ID NOs 4 and 5).

One of skill in the art would understand that pharmaceutical compositions containing BAFF- or APRIL-relevant compositions can be used in combination with each other or in sequence with each other. One of skill in the art would understand that any methods applicable for designing compositions relating to BAFF are also applicable for designing compositions relating to APRIL.

In some embodiments, the interaction between BAFF and a receptor is enhanced by overexpression of one or more of the receptors. For example, it has been shown that IFN-γ promotes BAFF-R promoter activity and up-regulates BAFF-R mRNA expression. See Yuan, H. et al., 2010, "Characterization of the 5'-flanking region and regulation of transcription of human BAFF-R gene," *DNA Cell Biol.* 29(3):133-139, which is hereby incorporated by reference herein in its entirety.

In some embodiments, the interaction between BAFF and a receptor is enhanced by removing an inhibitor or a molecule that interferes with the interaction. For example, BAFF-R appears to be selective for BAFF, but APRIL competes with BAFF in binding to TACI and BCMA. In some embodiments, the interaction between BAFF and TACI or BCMA will be enhanced by selectively removing the interference from APRIL. See, Schneider, P. and Tschopp, J., 2003, "BAFF and the regulation of B cell survival," *Immunology Letters* 88(1): 57-62, which is hereby incorporated by reference herein in its entirety. In some embodiments, antibodies targeting APRIL can be used to enhance the interaction between BAFF and a receptor.

In some embodiments, the antibody targeting a receptor of BAFF or the BAFF-receptor complex is a monoclonal antibody or a polyconal antibody. In some embodiments, the interaction between BAFF and a receptor is enhanced by prolonging the interaction. For example, a molecule can be added to prevent the dissociation of the BAFF-receptor complex in order to substantiate the downstream effects, such as protection against weight gain and/or glucose dysmetabolism.

In alternative embodiments, analogues of BAFF can be added which would bind to one or more the BAFF receptors to initiate the desired downstream events. The analogue of BAFF can be a peptide based on one of more functional sequences of BAFF. In some embodiments, peptide analogues of BAFF are used, which comprises one or more chemical modifications and/or sequence modification such that the peptide analogues are no longer identical to the natural sequence of BAFF.

In some embodiments, also provided herewith are methods and systems for identifying factors that interact with BAFF. As mentioned above, BAFF is the natural ligand of three TNF receptors, namely the BAFF receptor (BAFF-R, or TNFRSF13), transmembrane activator and calcium modulator and cyclophilin ligand interactor (TACI), and B-cell maturation antigen (BCMA), all of which have differing binding affinities for it. All three receptors have recently been shown to be expressed by human adipocytes (both white and brown), as well as by mouse adipocyte cell lines.

In some embodiments, a pharmaceutical composition, such as recombinant BAFF, can be introduced directly to an animal or a human subject. The manner of administration of a pharmaceutical composition of the present invention can depend upon the particular purpose for the delivery (e.g. treatment of disease or prevention of graft rejection), the overall health and condition of the recipient and the judgment of the physician or technician administering the pharmaceutical composition. A pharmaceutical composition of the present invention can be administered to an animal using a variety of methods. Such delivery methods can include parenteral, topical, oral, or local administration, such as intradermally or by aerosol. A pharmaceutical composition can be administered in a variety of unit dosage forms depending upon the method of administration. For example, unit dosage forms suitable for oral administration to the intestinal region of an animal include powders, tablets, pills, and capsules. Preferred delivery methods for a pharmaceutical composition of the present invention include intravenous administration and local administration by, for example, injection or topical administration. Injection can be, for example, intraperitoneal injection and/or subcutaneous injection. For particular modes of delivery, a pharmaceutical composition of the present invention can be formulated in an excipient of the present invention. A therapeutic reagent of the present invention can be administered to any animal, preferably to mammals, and more preferably to humans.

In some embodiments, a pharmaceutical composition of the present invention is administered by itself. Alternatively, a pharmaceutical composition of the present invention is administered in combination with other therapeutic reagents. In some embodiments, multiple pharmaceutical compositions can be administered in combination with each other. For example, multiple BAFF peptides and/or peptide analogues can be used in combination with each other. In some embodiments, one or more peptides and/or peptide analogues targeting APRIL can be used in combination with those targeting BAFF.

In some embodiments, a pharmaceutical composition of the present invention is delivered as part of a "drug delivery system" or the like. For example, a pharmaceutical composition of the present invention refers to a unit dosage form of a drug or agent composition, preferably any compositions comprising combinations of at least two or more agents, including carriers, enhancers, and other components, in which the multi-agent compound is contained in or accompanied by means for maintaining the drug composition in a drug transferring relationship or providing any multi-agent compounds to the desired site in the body. Such means can be a patch, tablet, troche, or other device of determined physical form for continuous agent administration thereto for systemic transport, or such means can be formulated in free form to be applied directly to the patient as a cream, gel, gum, ointment, or the like.

In some embodiments, a pharmaceutical composition of the present invention further includes pharmaceutically acceptable adjuvants and/or carriers. The compositions may also include other medicinal agents, pharmaceutical agents, carriers, adjuvants, diluentss and other pharmaceutical preparations known to those skilled in the art. Such agents are known to those skilled in the art and are generally described as being biologically inactive and can be administered to patients without causing deleterious interactions with the therapeutic agent. Examples of carriers or excipients for oral administration include corn starch, lactose, magnesium stearate, microcrystalline cellulose, stearic acid, povidone, dibasic calcium phosphate, and sodium starch glycolate. Any carrier suitable for the desired administration route is contemplated by the present invention. Additional examples of acceptable adjuvants and/or carriers include but are not limited to hydroxypropyl cellulose, hydroxypropyl methylcellulose, hydroxy ethylcellulose, ethylcellulose, carboxymethyl cellulose, dextran, guar gum, polyvinyl pyrrolidone, pectins, starches, gelatin, casein, acrylic acid polymers, polymers of acrylic acid esters, acrylic acid copolymers, vinyl polymers, vinyl copolymers, polymers of vinyl alcohols, alkoxy polymers, polyethylene oxide polymers, polyethers, and mixtures thereof and the like.

In some embodiments, peptides and/or analogues of BAFF or APRIL of the present invention are delivered to a subject (e.g. a human in need of treatment or at risk of developing obesity) by using one or more nucleic acids encoding the corresponding amino acid sequence.

Additional receptors and ligand interactions can also be used to modulate thermogenesis by brown fat and can be identified by a combination of biochemical and genetic analysis. For example, DNA microarray technology can be used to identify proteins that are regulated by BAFF and APRIL signaling in brown fat and can also be used to identify downstream effectors post BAFF-receptor interactions.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Functional Analysis of RP105

RP105, which has been described as a B-cell-specific molecule that drives proliferation when cross-linked by antibodies, was studied, with results showing that: (a) RP105 expression mirrors that of TLRs on myeloid and other cells; and (b) RP105 inhibits TLR4 signaling in primary myeloid cells and cell lines and regulates in vivo responses to LPS. Preliminary data indicate that RP105 also regulates energy metabolism in response to caloric excess. The present experiments also showed that RP105-deficient mice are protected from obesity and glucose dysmetabolism.

Six to eight week-old male C57BL/6 RP105−/− mice and wild type (WT) controls were placed on a high fat diet (HFD) or a regular chow diet (RD). As shown in FIG. 1A, RP105-deficient mice gain significantly less weight than WT controls when subjected to HFD stress. RP105−/− mice eat the same amount as WT controls on a HFD and have identical food absorption data (as quantified by bomb calorimetry), which is indicative of an effect on the regulation of energy metabolism.

Figure 1B:
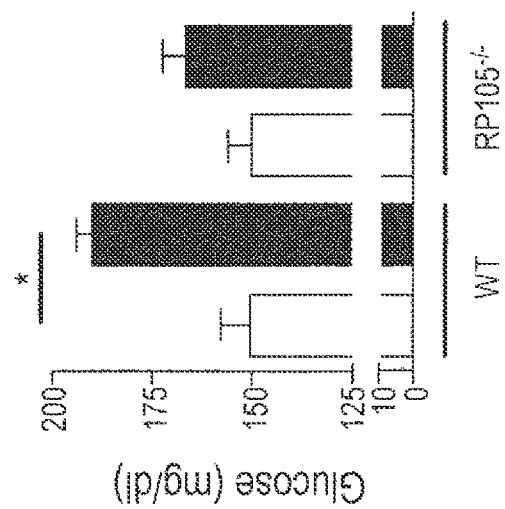

Adaptive thermogenesis by brown fat, which occurs in response to cold stress as well as dietary excess, is dependent on the expression of UCP1. The data demonstrate that: (a) brown fat from RP105−/− mice on a HFD express significantly more UCP1 compared to WT controls (data not shown); and (b) the obesity phenotype of RP105−/− mice on a HFD is even more robust under thermoneutral conditions. The latter finding suggests that the relevant variable is dietary excess, rather than the cold stress associated with standard housing. As might be expected, in parallel with protection from obesity, RP105−/− mice are protected from the metabolic and end-organ sequelae of obesity, including glucose dysmetabolism (as shown in FIG. 1B), dyslipidemia, and hepatic steatosis. These effects upstream of the development of obesity are compatible with the described role of TLRs in driving these downstream sequelae.

FIG. 1B shows fasting glucose levels, quantified after the mice had been on a designated diet for 10 weeks. After an 8 hour fast, blood glucose levels were quantified by glucometer. RD results are depicted by white bars; HFD results are depicted by black bars. Data represent means+SE in a single experiment, representative of 10 individual experiments; n=10-14 mice/group. For FIG. 1A, AUC ANOVA P<0.01, Tukey's correction ***P<0.001; for FIG. 1B, ANOVA P<0.0001, Tukey's correction *P<0.01.

Example 2

Effect of RP105 on LPS-Driven B-Cell Proliferation

Figures 2A, 2B:
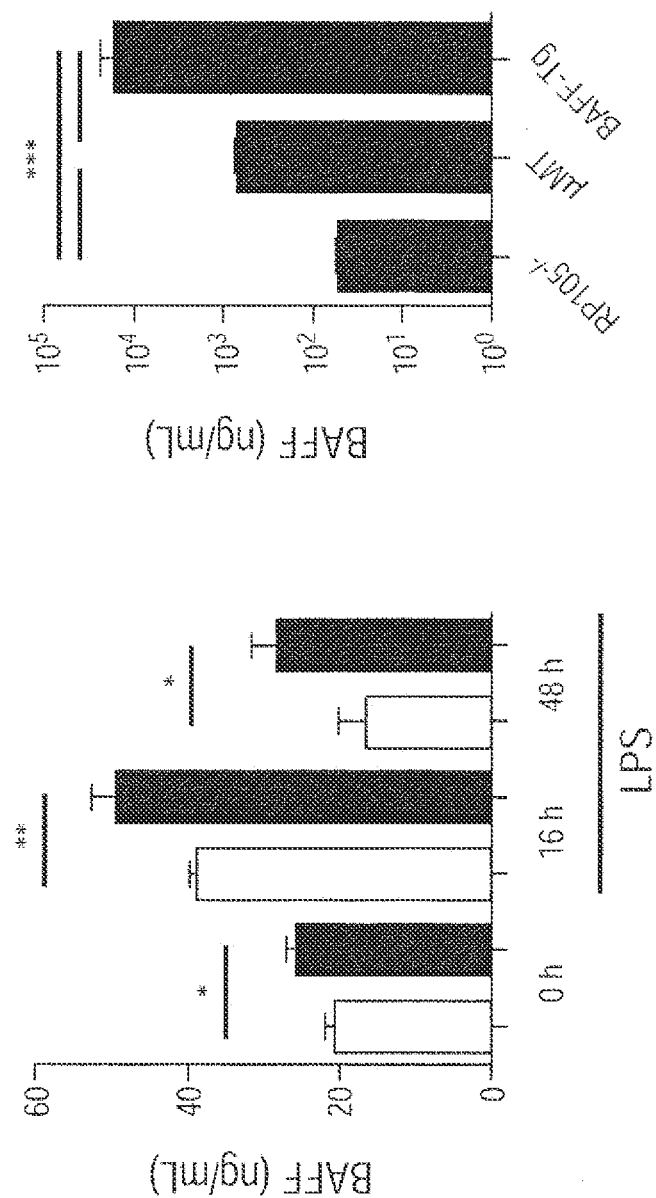
FIGS. 2A-B illustrates the comparison between serum BAFF levels in RP105−/−, μMT and BAFF-Tg mice.

RP105-deficient mice exhibit blunted LPS-driven B cell-proliferation, something that had been interpreted to indicate that RP105 facilitates TLR4 signaling in B-cells. Given the fact that RP105 inhibits TLR4 signaling in other cells, the role of RP105 in B-cell function was re-examined. It was found that: (a) modulation of TLR4-driven B-cell proliferative responses by RP105 is not a function of B-cell-intrinsic expression of RP105; and (b) a mechanistic role for dysregulated BAFF expression was demonstrated. As RP105−/− mice exhibit significantly increased basal and TLR-driven BAFF expression (as shown in FIG. 2A), transgenic overexpression of BAFF recapitulates the impaired TLR4-driven proliferation by RP105−/− B-cells, and partial neutralization of BAFF rescues the aberrant B-cell proliferative responses of RP105−/− mice. These data also elucidate into the role of RP105 in regulating energy metabolism.

BAFF was discovered for its role in B-cell maturation and survival. BAFF overexpression augments B-cell numbers and can lead to the development of B-cell-dependent autoimmune disease. In contrast, genetic deletion or antibody-mediated inhibition of BAFF results in contraction of the B-cell compartment. BAFF is produced by diverse myeloid, lymphoid and stromal cell types, including adipocytes.

FIG. 2 illustrates the comparison among serum BAFF levels in RP105−/−, μMT, and BAFF-Tg mice. Among other stimuli, TLR signaling induced BAFF expression (as shown in FIG. 2A). For the kinetic analysis, mice were mock-challenged or challenged with TLR4-specific E. coli LPS (40 μg, i.p.), and serum BAFF levels were determined kinetically.

BAFF binds to 3 receptors, namely the BAFF receptor (BAFF-R), transmembrane activator and calcium modulator and cyclophilin ligand interactor (TACI), and B-cell maturation antigen (BCMA). All 3 receptors have recently been shown to be expressed by human adipocytes (both white and brown), as well as by mouse adipocyte cell lines.

Example 3

Effect of BAFF Concentration

BAFF overexpression was shown to be associated with protection from weight gain and glucose dysmetabolism. In the experiments shown in FIG. 3, six to eight week-old male μMT, BAFF-transgenic, and WT mice (all on a C57BL/6 background) were placed on a HFD or RD.

B-cell-deficient (μMT) mice exhibited robust secondary increases in circulating BAFF concentrations (in response to the lack of B-cells), and BAFF-transgenic (BAFF-Tg) mice had extremely robust serum BAFF levels (FIG. 2B). The responses of these mice to HFD stress were defined.

Similar to RP105−/− mice (as shown in FIG. 1), μMT and BAFF-Tg mice were significantly protected from developing obesity on a HFD (as shown in FIGS. 3A and 3C). In these experiments, (a) mouse weight correlated directly with adiposity (data not shown); and (b) protection from obesity was associated with protection from glucose dysmetabolism (as shown in FIGS. 3B and 3D). FIGS. 3B and 3D depict fasting glucose levels, quantified after the mice had been on a designated diet for 9 weeks.

Example 4

Response to HFD Stress

Figure 4:
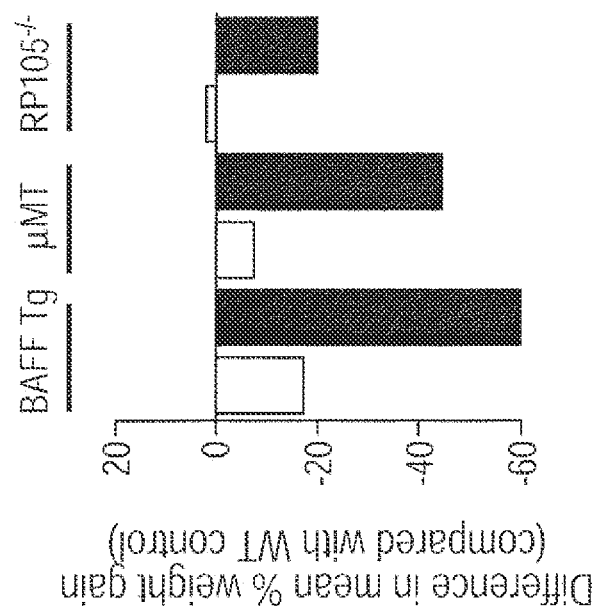
FIG. 4 illustrates the comparison of the response to HFD stress across genotypes. The figure depicts the difference in mean percent weight gain (compared with WT controls) after 12 weeks on the diet in mice; data were taken from the experiments depicted in FIGS. 1 and 3. RD results are represented by white bars; HFD results are represented by black bars.

In comparison with WT mice, genetically modified mice with higher levels of BAFF showed more resistance to weight gain when they were subjected to the stress of a HFD. The data suggest an approximate log-linear dose response in terms of the effects of circulating BAFF levels on weight gain. For example, FIG. 2B shows that μMT mice exhibited serum BAFF levels 1.5 log higher than that of the RP105−/− mice, and BAFF-Tg mice exhibited a further 1.5 log elevation in serum BAFF levels. FIG. 4 further demonstrates that the difference in levels of BAFF correlate with differences in weight gain by the different types of mice. These data indicate that the modest elevations of BAFF observed in RP105−/− mice were sufficient for significant effects on obesity.

Example 5

Brown Adipocyte Respiration

Figure 5:
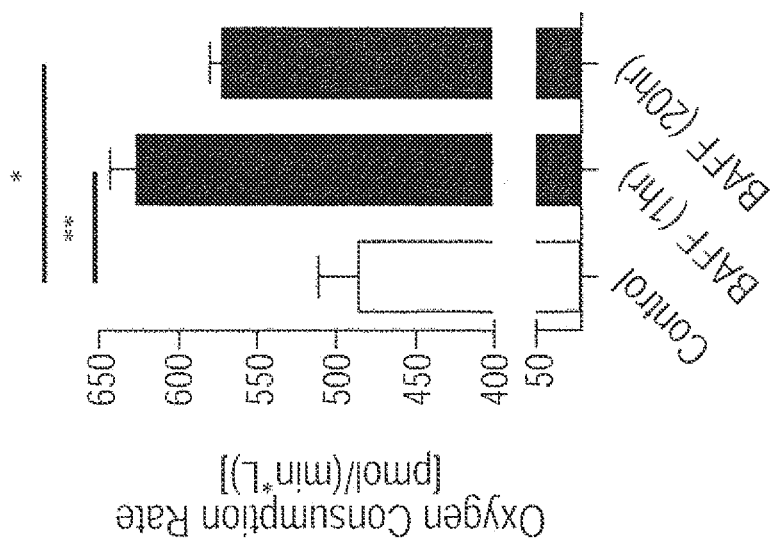
FIG. 5 illustrates that BAFF stimulates brown adipocyte respiration in vitro. An immortalized mouse brown adipocyte cell line was differentiated and subsequently stimulated with rBAFF (2 μg/ml) or mock-stimulated, and the oxygen consumption rate was quantified using an XF24 extracellular flux analyzer (Seahorse Bioscience, North Billerica, Mass.) at the times indicated after BAFF addition; all conditions were measured at the same time. Data represent means+SE in a single experiment; ANOVA P<0.005, Tukey's correction *P<0.05, **P<0.01.

Given the data on BAFF expression and the response to HFD stress, the data indicating increased UCP1 expression by brown fat from RP105−/− mice on a HFD, and recent reports of BAFF receptor expression by brown fat, the potential direct effects of BAFF on brown adipocyte respiration were studied. As shown in FIG. 5, in vitro treatment of an adipocyte cell line with recombinant BAFF resulted in rapid up-regulation in respiration by brown adipocytes.

Example 6

Analysis of Brown Fat Mitochondria

Figure 6:
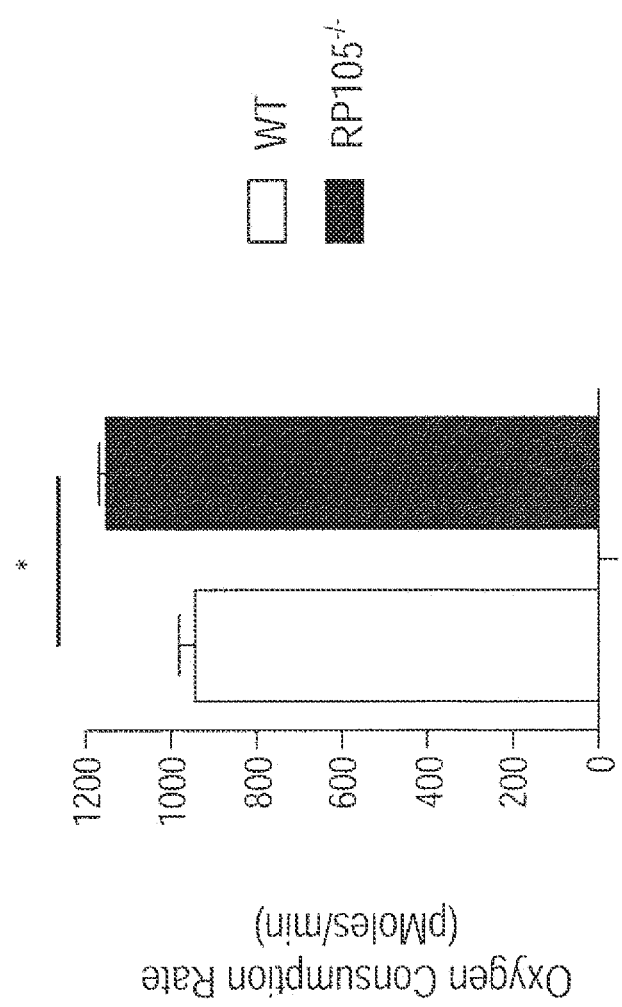
FIG. 6 illustrates that brown fat mitochondria from RP105-deficient mice exhibit increased uncoupled respiration. WT and RP105−/− C57BL/6 male mice were fed a HFD for 24 weeks. Uncoupled respiration (pyruvate/malate induced, GDP inhibitable respiratory activity) was quantified in mitochondria isolated from brown adipose tissue using an XF24 extracellular flux analyzer (Seahorse Bioscience). WT results are represented by white bars; RP105−/− results are represented by black bars. Data represent means+ SE, normalized to Vmax (oxygen consumption driven by FCCP); n=4 mice/group; *P=0.002 (Student's t test).

Brown fat mitochondria from RP105-deficient mice exhibit increased uncoupled respiration (as shown in FIG. 6). WT and RP105−/− C57BL/6 male mice were fed a HFD for 24 weeks. Uncoupled respiration (pyruvate/malate-induced, GDP inhibitable respiratory activity) was quantified in mitochondria isolated from brown adipose tissue using an XF24 extracellular flux analyzer (Seahorse Bioscience).

Example 7

Increased Norepinephrine-Induced Thermogenesis in RP105-Deficient Mice

Adaptive thermogenesis was compared in RP105−/− and WT mice on a HFD. RP105−/− and WT mice, both on a C57BL/6 background, were placed on a HFD (60% kcal from fat, 20% kcal from carbohydrate, 20% kcal from protein, Research Diets #D12492i) for 14 days. Mice were anaesthetized by intraperitoneal injection of ketamine/xylazine, and the basal rate of oxygen consumption (at 33° C.) was quantified kinetically, at 3 minute intervals for 24 minute, by indirect calorimetry. Oxygen consumption continued to be quantified kinetically after subsequent subcutaneous challenge, depicted on FIG. 8 with an arrow, with 1 mg/kg norepinephrine bitartrate. WT results are represented by open symbols; RP105−/− results are represented by closed symbols. Data represent means+/−SE of an n=4-5 mice/experimental group; t test; * $P<0.05$.

Example 8

Up-Regulated Norepinephrine-Induced Thermogenesis as a Result of BAFF Treatment

WT C57BL/6 mice were placed on either a HFD (60% kcal from fat, 20% kcal from carbohydrate, 20% kcal from protein, Research Diets #D12492i) or a RD (chow; 13.5% kcal from fat, 59% kcal from carbohydrate, 27.5% kcal from protein, Lab Diet #5010) for 14 days. Mice were subsequently given 1 mg/kg recombinant BAFF or vehicle control (saline) by intraperitoneal injection 18 hours and 2 hours prior to quantification of oxygen consumption. Mice were then anaesthetized by intraperitoneal injection of ketamine/xylazine, and the basal rate of oxygen consumption (at 330 C) was quantified kinetically, at 5 minute intervals for 25 minutes, by indirect calorimetry. Oxygen consumption continued to be quantified kinetically after subsequent subcutaneous challenge, depicted on FIG. 9 with an arrow, with 1 mg/kg norepinephrine bitartrate. RD+saline results are represented by open squares; RD+BAFF results are represented by closed squares; HFD+saline results are represented by open circles; HFD+BAFF results are represented by closed circles. Data represent single mice/experimental group.

Example 9

Figure 10:
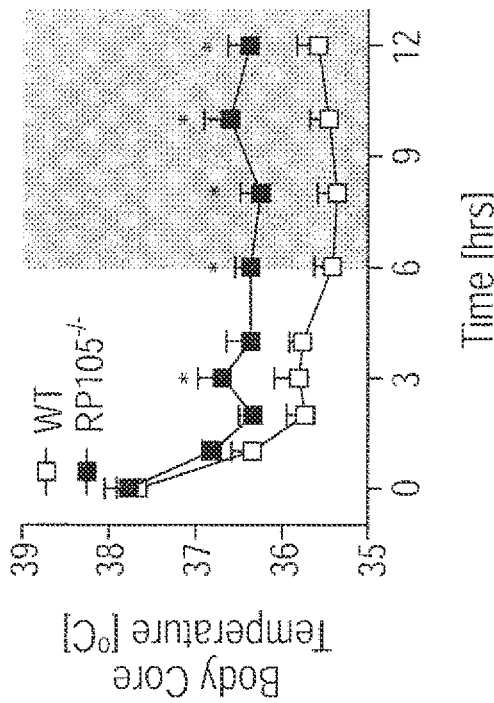
FIG. 10 illustrates that RP105-deficient mice maintain body core temperature better during cold exposure. Six to eight week-old male C57BL/6 RP105$^{-/-}$ mice and WT controls were placed on a HFD for 16 weeks. Animals were subsequently placed at 4° C., and body core temperature was quantified. The mice were then subjected to 0-6 hours of cold exposure, under lighted conditions; 6-12 hours cold exposure was conducted under dark conditions. WT HFD results are represented by white squares; RP105$^{-/-}$ HFD results are represented by black squares. Data represent means+SE in a single experiment, representative of 2 individual experiments; n=5-6 mice/group; *P<0.05 (Student's t test).

Improved Maintenance of Body Core Temperature by RP105-Deficient Mice During Cold Exposure The ability of RP105-deficient mice to maintain body core temperature during cold exposure was studied. Six to eight week-old male C57BL/6 RP105−/− mice and WT controls were placed on a HFD for 16 weeks. Animals were subsequently placed at 4° C., and body core temperature was quantified. The mice were then subjected to 0-6 hours of cold exposure, under lighted conditions; 6-12 hours cold exposure was conducted under dark conditions. FIG. 10 illustrates that RP105-deficient mice maintain body core temperature better during cold exposure. WT HFD results are represented by white squares; RP105−/− HFD results are represented by black squares. All data represent means+SE in a single experiment, representative of 2 individual experiments; n=5-6 mice/group; *$P<0.05$ (Student's t test).

Example 10

Increased UCP-1 Expression in Brown Adipose Tissue of RP105-Deficient Mice

Figure 11:
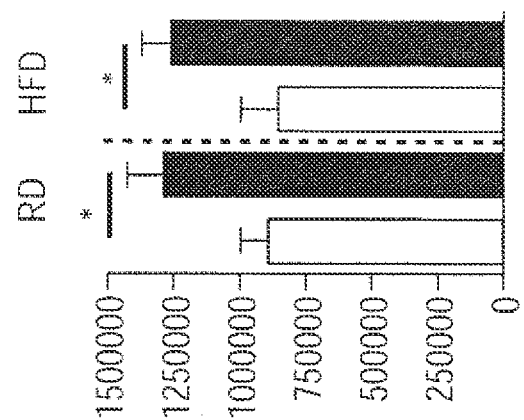
FIG. 11 illustrates that RP105-deficient mice have increased uncoupling protein 1 (UCP-1) expression in brown adipose tissue. Six to eight week-old male C57BL/6 RP105$^{-/-}$ mice and wild type (WT) controls were placed on a regular diet (RD) or a high fat diet (HFD) for 20 weeks, and UCP-1 expression was quantified by qRT-PCR. WT results are represented by white bars; RP105$^{-/-}$ results are represented by black bars. Data represent means+SE in a single experiment, representative of 2 individual experiments; n=6 mice/group; *P<0.05 (Student's t test).

The expression of UCP-1 in the brown adipose tissue of RP105-deficient mice was then studied. Six to eight week-old male C57BL/6 RP105−/− mice and wild type (WT) controls were placed on a regular diet (RD) or a high fat diet (HFD) for 20 weeks, and UCP-1 expression was quantified by qRT-PCR. FIG. 11 illustrates that RP105-deficient mice have increased uncoupling protein 1 (UCP-1) expression in brown adipose tissue. WT results are represented by white bars; RP105−/− results are represented by black bars. All data represent means+SE in a single experiment, representative of 2 individual experiments; n=6 mice/group; *$P<0.05$ (Student's t test).

The various methods and techniques described above provide a number of ways to carry out the invention. Those skilled in the art will recognize that the methods can be performed in a manner that achieves or optimizes one advantage or group of advantages as taught herein without necessarily achieving other objectives or advantages as may be taught or suggested herein. It is to be understood that some embodiments specifically include one, another, or several features, while others specifically exclude one, another, or several features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of treating obesity and/or one or more sequelae thereof in a subject, comprising:
administering to a subject in need of treatment for obesity and/or one or more sequelae thereof, a therapeutically effective amount of a pharmaceutical composition to enhance thermogenesis associated with brown fat or brown fat cells,
wherein said pharmaceutical composition comprises a proliferation-inducing ligand (APRIL) protein, a recombinant APRIL protein, or an agonistic variant thereof.

2. The method of claim 1, wherein thermogenesis associated with brown fat or brown fat cells comprises thermogenesis by brown fat or brown fat cells, adaptive thermogenesis by brown fat or brown fat cells, thermogenic capacity of brown fat or brown fat cells, or a combination thereof.

3. The method of claim 1, wherein thermogenesis associated with brown fat or brown fat cells is enhanced by increasing the level or activity of APRIL.

4. The method of claim 1, wherein said pharmaceutical composition comprises a recombinant APRIL protein.

5. The method of claim 1, wherein said pharmaceutical composition is administered to a subject via parenteral, topical, oral, or local administration, injection, or a combination thereof.

6. The method of claim 5, wherein said subject is a human in need of treatment for obesity and/or one or more sequelae thereof.

7. The method of claim 1, wherein said pharmaceutical composition comprises an agonistic variant of a recombinant APRIL protein.

8. The method of claim 1, wherein said pharmaceutical composition comprises an APRIL protein or a recombinant APRIL protein.

9. The method of claim 1, wherein said pharmaceutical composition comprises a recombinant APRIL protein or an agonistic variant thereof.

10. The method of claim 1, wherein said pharmaceutical composition is administered to a subject via parenteral, topical, oral, or local administration.

11. The method of claim 1, wherein said pharmaceutical composition is administered to a subject by injection, intraperitoneal injection, or subcutaneous injection.

12. A method of treating obesity and/or one or more sequelae thereof in a subject, comprising:
administering to a subject in need of treatment for obesity and/or one or more sequelae thereof, a therapeutically effective amount of a pharmaceutical composition,
wherein said pharmaceutical composition comprises a proliferation-inducing ligand (APRIL) protein or a recombinant APRIL protein.

13. The method of claim 12, wherein the administering enhances thermogenesis associated with brown fat or brown fat cells; and
thermogenesis associated with brown fat or brown fat cells comprises thermogenesis by brown fat or brown fat cells, adaptive thermogenesis by brown fat or brown fat cells, thermogenic capacity of brown fat or brown fat cells, or a combination thereof.

14. The method of claim 12, wherein the administering enhances thermogenesis associated with brown fat or brown fat cells; and
thermogenesis associated with brown fat or brown fat cells is enhanced by increasing the level or activity of APRIL.

15. The method of claim 12, wherein said pharmaceutical composition comprises a recombinant APRIL protein.

16. The method of claim 12, wherein said pharmaceutical composition is administered to a subject via parenteral, topical, oral, or local administration, injection, or a combination thereof.

17. The method of claim 12, wherein said subject is a human in need of treatment for obesity and/or one or more sequelae thereof.

18. The method of claim 12, wherein said pharmaceutical composition is administered to a subject via parenteral, topical, oral, or local administration.

19. The method of claim 12, wherein said pharmaceutical composition is administered to a subject by injection, intraperitoneal injection, or subcutaneous injection.

* * * * *

SEQUENCE LISTING

```
<160> NUMBER OF SEQ ID NOS: 5

<210> SEQ ID NO 1
<211> LENGTH: 285
<212> TYPE: PRT
<213> ORGANISM: Homo sapiens

<400> SEQUENCE: 1

Met Asp Asp Ser Thr Glu Arg Glu Gln Ser Arg Leu Thr Ser Cys Leu
 1               5                  10                  15

Lys Lys Arg Glu Glu Met Lys Leu Lys Glu Cys Val Ser Ile Leu Pro
             20                  25                  30

Arg Lys Glu Ser Pro Ser Val Arg Ser Ser Lys Asp Gly Lys Leu Leu
         35                  40                  45

Ala Ala Thr Leu Leu Leu Ala Leu Leu Ser Cys Cys Leu Thr Val Val
     50                  55                  60

Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125
```

```
Ser Arg Asn Lys Arg Ala Val Gln Gly Pro Glu Glu Thr Val Thr Gln
            130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
                195                 200                 205

Gly His Leu Ile Gln Arg Lys Lys Val His Val Phe Gly Asp Glu Leu
            210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
            275                 280                 285

<210> SEQ ID NO 2
<211> LENGTH: 266
<212> TYPE: PRT
<213> ORGANISM: Homo sapiens

<400> SEQUENCE: 2

Met Asp Asp Ser Thr Glu Arg Glu Gln Ser Arg Leu Thr Ser Cys Leu
 1               5                  10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
            85                  90                  95

Ala Pro Lys Ala Gly Leu Glu Glu Ala Pro Ala Val Thr Ala Gly Leu
        100                 105                 110

Lys Ile Phe Glu Pro Pro Ala Pro Gly Glu Gly Asn Ser Ser Gln Asn
    115                 120                 125

Ser Arg Asn Lys Arg Ala Val Gln Gly Pro Glu Glu Thr Gly Ser Tyr
            130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
                165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
        195                 200                 205

Thr Leu Phe Arg Cys Ile Gln Asn Met Pro Glu Thr Leu Pro Asn Asn
    210                 215                 220
```

Ser Cys Tyr Ser Ala Gly Ile Ala Lys Leu Glu Gly Asp Glu Leu
225                 230                 235                 240

Gln Leu Ala Ile Pro Arg Glu Asn Ala Gln Ile Ser Leu Asp Gly Asp
                245                 250                 255

Val Thr Phe Phe Gly Ala Leu Lys Leu Leu
            260                 265

<210> SEQ ID NO 3
<211> LENGTH: 309
<212> TYPE: PRT
<213> ORGANISM: Mus musculus

<400> SEQUENCE: 3

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
                20                  25                  30

Gln Lys Glu Glu Gly Ala Trp Phe Gly Ile Cys Arg Asp Gly Arg Leu
            35                  40                  45

Leu Ala Ala Thr Leu Leu Leu Ala Leu Leu Ser Ser Ser Phe Thr Ala
50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
    130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
            260                 265                 270

Gly Ile Ala Arg Leu Glu Glu Gly Asp Glu Ile Gln Leu Ala Ile Pro
        275                 280                 285

Arg Glu Asn Ala Gln Ile Ser Arg Asn Gly Asp Asp Thr Phe Phe Gly
    290                 295                 300

Ala Leu Lys Leu Leu
305

-continued

```
<210> SEQ ID NO 4
<211> LENGTH: 250
<212> TYPE: PRT
<213> ORGANISM: Homo sapiens

<400> SEQUENCE: 4

Met Pro Ala Ser Ser Pro Phe Leu Leu Ala Pro Lys Gly Pro Pro Gly
  1               5                  10                  15

Asn Met Gly Gly Pro Val Arg Glu Pro Ala Leu Ser Val Ala Leu Trp
             20                  25                  30

Leu Ser Trp Gly Ala Ala Leu Gly Ala Val Ala Cys Ala Met Ala Leu
         35                  40                  45

Leu Thr Gln Gln Thr Glu Leu Gln Ser Leu Arg Arg Glu Val Ser Arg
     50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                 85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 240
<212> TYPE: PRT
<213> ORGANISM: Mus musculus

<400> SEQUENCE: 5

Met Pro Ala Ser Ser Pro Gly His Met Gly Gly Ser Val Arg Glu Pro
  1               5                  10                  15

Ala Leu Ser Val Ala Leu Trp Leu Ser Trp Gly Ala Val Leu Gly Ala
             20                  25                  30

Val Thr Cys Ala Val Ala Leu Leu Ile Gln Gln Thr Glu Leu Gln Ser
         35                  40                  45

Leu Arg Arg Glu Val Ser Arg Leu Gln Arg Ser Gly Gly Pro Ser Gln
     50                  55                  60

Lys Gln Gly Glu Arg Pro Trp Gln Ser Leu Trp Glu Gln Ser Pro Asp
 65                  70                  75                  80

Val Leu Glu Ala Trp Lys Asp Gly Ala Lys Ser Arg Arg Arg Arg Ala
```

-continued

```
                85                  90                  95
Val Leu Thr Gln Lys His Lys Lys His Ser Val Leu His Leu Val
            100             105             110

Pro Val Asn Ile Thr Ser Lys Asp Ser Asp Val Thr Glu Val Met Trp
        115             120             125

Gln Pro Val Leu Arg Arg Gly Arg Gly Leu Glu Ala Gln Gly Asp Ile
    130             135             140

Val Arg Val Trp Asp Thr Gly Ile Tyr Leu Leu Tyr Ser Gln Val Leu
145             150             155             160

Phe His Asp Val Thr Phe Thr Met Gly Gln Val Val Ser Arg Glu Gly
                165             170             175

Gln Gly Arg Arg Glu Thr Leu Phe Arg Cys Ile Arg Ser Met Pro Ser
            180             185             190

Asp Pro Asp Arg Ala Tyr Asn Ser Cys Tyr Ser Ala Gly Val Phe His
        195             200             205

Leu His Gln Gly Asp Ile Ile Thr Val Lys Ile Pro Arg Ala Asn Ala
    210             215             220

Lys Leu Ser Leu Ser Pro His Gly Thr Phe Leu Gly Phe Val Lys Leu
225             230             235             240
```